(12) United States Patent
Araci et al.

(10) Patent No.: US 11,707,739 B2
(45) Date of Patent: Jul. 25, 2023

(54) CONTINUOUS MICROFLUIDIC DILATOMETRY FOR PHYSICAL ACTIVITY MONITORING WITH ULTRAHIGH SENSITIVITY

(71) Applicant: Santa Clara University, Santa Clara, CA (US)

(72) Inventors: Ismail Emre Araci, Santa Clara, CA (US); Laura Rivas Yepes, Mountain View, CA (US)

(73) Assignee: Santa Clara University, Santa Clara, CA (US)

(*) Notice: Subject to any disclaimer, the term of this patent is extended or adjusted under 35 U.S.C. 154(b) by 479 days.

(21) Appl. No.: 17/063,290

(22) Filed: Oct. 5, 2020

(65) Prior Publication Data
US 2021/0106995 A1    Apr. 15, 2021

Related U.S. Application Data

(60) Provisional application No. 62/914,430, filed on Oct. 12, 2019.

(51) Int. Cl.
*B01L 3/00*      (2006.01)
*G01F 1/36*      (2006.01)
*G01F 5/00*      (2006.01)

(52) U.S. Cl.
CPC ........ *B01L 3/502715* (2013.01); *G01F 1/363* (2013.01); *G01F 5/005* (2013.01); *B01L 2300/0883* (2013.01); *B01L 2400/0406* (2013.01)

(58) Field of Classification Search
CPC ....... B01L 3/502715; B01L 2300/0883; B01L 2400/0406; G01F 1/363; G01F 5/005; G01F 9/00; A61B 5/1118; A61B 5/6801; G01B 7/18; G01B 13/24
See application file for complete search history.

(56) References Cited

U.S. PATENT DOCUMENTS

| | | | | |
|---|---|---|---|---|
| 8,292,798 | B2* | 10/2012 | Califorrniaa | C12M 25/00 600/33 |
| 10,898,074 | B2* | 1/2021 | Araci | G02C 7/04 |
| 2015/0057593 | A1* | 2/2015 | Johnson | A61F 9/00781 604/9 |
| 2016/0015265 | A1* | 1/2016 | Mandel | A61B 90/361 600/403 |
| 2019/0076021 | A1* | 3/2019 | Araci | G02C 7/04 |
| 2021/0129141 | A1* | 5/2021 | Sadabadi | B01L 3/502715 |

* cited by examiner

*Primary Examiner* — Manuel A Rivera Vargas
*Assistant Examiner* — Yaritza H Perez Bermudez
(74) *Attorney, Agent, or Firm* — Lumen Patent Firm

(57) ABSTRACT

Continuous microfluidic dilatometry devices and methods are provided for activity monitoring with ultra-high sensitivity. Corner flow in capillary channels is used to detect the resistance change in microfluidic circuits filled with ionic liquids. The conversion of mechanical input (e.g. strain) to an intermediary domain, namely liquid displacement, allows a large enhancement in sensor performance. Embodiments are suitable for tracking skin deformations that occur as a result of human movements.

3 Claims, 18 Drawing Sheets

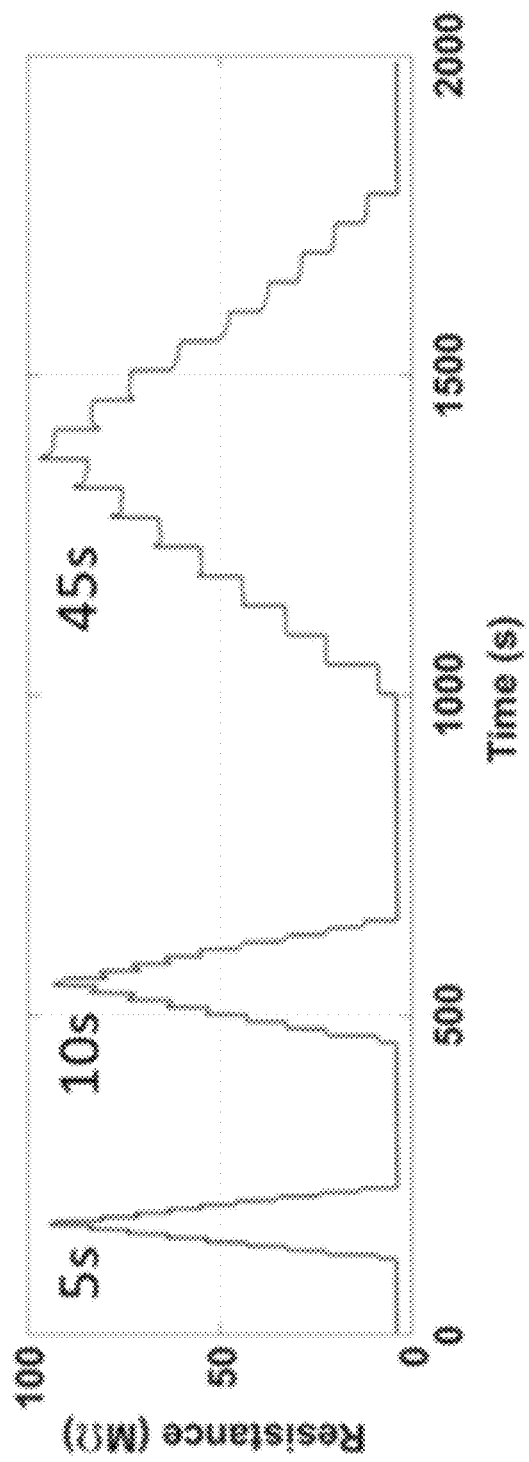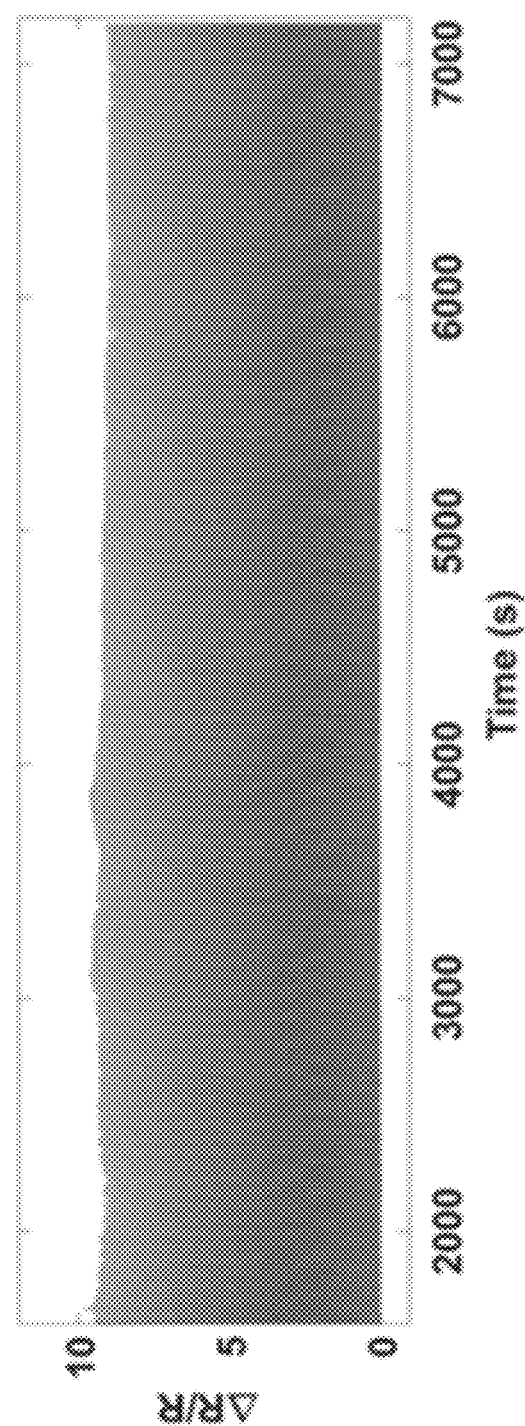

CONTINUOUS MICROFLUIDIC DILATOMETRY FOR PHYSICAL ACTIVITY MONITORING WITH ULTRAHIGH SENSITIVITY

CROSS-REFERENCE TO RELATED APPLICATIONS

This application claims priority from U.S. Provisional Patent Application 62/914,430 filed Oct. 12, 2019, which is incorporated herein by reference.

FIELD OF THE INVENTION

This invention relates to microfluidic dilatometry devices and methods.

BACKGROUND OF THE INVENTION

Standard elastomeric strain sensors (e.g. conductive bands, microfluidic channels filled with ionic liquids) directly convert strain to an electrical domain and measure the resistance change due to the length and cross-sectional area change of the sensor. We have shown that the strain can be converted to a liquid displacement in an optimized microfluidic circuit under the principle of microfluidic dilatometry. This liquid displacement can be measured using imaging techniques for a highly sensitive sensor however such an imaging approach is not practical for continuous measurements. The present invention addresses these shortcomings and provides a new technology for continuous measurements.

SUMMARY OF THE INVENTION

Technology is provided that converts the liquid displacement in microfluidic channels to electrical or optical domain for continuous measurement of mechanical signals.

Embodiments of the invention use the corner flow in capillary channels to detect the resistance change in microfluidic circuits filled with ionic liquids. The conversion of mechanical input (e.g. strain) to an intermediary domain, namely liquid displacement, allows a large enhancement in sensor performance.

Particularly the sensitivity to applied tangential strain (both uniaxial and multiaxial) on thin stretchable substrates is enhanced, which provides a gauge factor much greater than standard microfluidic strain sensors.

Liquids mixed with colored dyes can also be used to convert the mechanical inputs to optical domain, which provides electromagnetic interference immunity and easy integration with other smart devices such as smartwatches.

According to these principles of the invention, embodiments are described herein. A first device converts the tangential strain to electrical domain. These sensors can be configured either for detection of linear strain or for the detection of area strain. The second device converts the tangential strain to optical domain.

In a first embodiment, a device and method are provided for measuring fluid flow. This method or device have a microfluidic network with a cross-sectional area of the microfluidic network defining 1 or more corners, and the microfluidic network contains an ionic or a conductive fluid.

An air or a nonconductive fluid supply is connected to the microfluidic network, and the air or the nonconductive fluid is in contact with the ionic or the conductive liquid.

A strain, a force or a pressure difference is applied to the microfluidic network. The strain, the force or the pressure causes a volume change of the microfluidic network volume. The volume change is proportional to the amount of applied strain, force or pressure, whereby a volume increase causes a decrease in pressure inside the microfluidic network hence pulling an air bubble or a nonconductive fluid into the microfluidic network, and vice versa. The (a) volume of air or the length of the air bubble, or the (b) volume of nonconductive fluid or the length of the nonconductive fluid entering the microfluidic network increases as the applied strain, force or pressure increases, and vice versa.

The air bubble or the nonconductive fluid causes the ionic or the conductive fluid to recede to the 1 or more corners of the microfluidic network and around the air bubble resulting in an electrical resistance change in the microfluidic network.

The method or device measures (a) or (b) which is proportional to the applied strain, force or pressure.

In a second embodiment, a device and method are provided for measuring strain. This method or device have a microfluidic network with a cross-sectional area of the microfluidic network defining 1 or more corners. The microfluidic network contains an ionic or a conductive fluid, and the microfluidic network defines a flow direction.

An air or a nonconductive fluid supply is connected to the microfluidic network, and the air or the nonconductive fluid is in contact with the ionic or the conductive liquid.

A strain is applied to the microfluidic network in a direction perpendicular to the flow direction of the microfluidic network. The strain causes a volume change of the microfluidic network volume, and the volume change is proportional to the amount of strain applied. A volume increase causes a decrease in pressure inside the microfluidic network hence pulling an air bubble into the microfluidic network, and vice versa.

The volume of air or the length of the air bubble entering the microfluidic network increases as the applied strain increases, and vice versa.

The air bubble causes the ionic or the conductive fluid to recede to the 1 or more corners of the microfluidic network and around the air bubble resulting in an electrical resistance change in the microfluidic network.

The method or device measures the electrical resistance change in the microfluidic network, where the resistance change is proportional to the applied strain.

In a third embodiment, a device and method are provided for measuring strain. This method or device have a microfluidic network a microfluidic network with a cross-sectional area of the microfluidic network defines 1 or more corners. The microfluidic network contains an optical fluid, and an optical fluid reservoir, and the microfluidic network defines a flow direction. An optical fluid open to a constant air pressure reservoir is provided.

A strain is applied to the microfluidic network in a direction perpendicular to the flow direction of the microfluidic network. The strain causes a volume change of the microfluidic network volume, and the volume change is proportional to the amount of strain applied. The volume increase causes a decrease in pressure inside the microfluidic network hence pulling the optical fluid from the optical fluid reservoir into the microfluidic network, and vice versa.

The volume of optical fluid or the length of the optical fluid entering the microfluidic network increases as the applied strain increases, and vice versa.

The optical fluid volume change causes the change in the optical path length in the optical reservoir.

The method or device measures an absorption change or a reflection change in the optical fluid reservoir, where the absorption or reflection change is proportional to the applied strain.

The embodiments of the invention have the following advantages and application. In the described embodiments, liquids with nearly zero Young's modulus are utilized. With this approach the need for less flexible metal, semiconductor, nanocomposite components as active sensor elements is eliminated.

With the described embodiments, a strong directional preference of the dilatometric response was demonstrated. This is achieved by controlling the channel elongation direction, whereas in nanoparticle-based strain sensors the nanowire elongation direction needs to be controlled for achieving directional preference, hence making the manufacturing process more complicated.

The sensitivity of the sensor is tunable and controlled by the device design and the ionic liquid contact angle as two independent strategies. The former strategy allows design of a sensor with the desired performance (e.g. sensitivity, dynamic range, etc.) without having to rely on material characteristics.

Finally, in the described invention paradigm, several dilatometric sensors can be integrated to interact in the fluidic domain hence fluidic signal processing can be realized without the need for a rigid integrated circuit (IC) as part of the wearable sensor.

Embodiments of the invention are suitable for tracking skin deformations that occur as a result of human movements. Therefore, tracking skin deformations could inform about the human movements. Tracking human movements have important applications in physiotherapy and physical rehabilitation, sports analytics, emotion monitoring, and human-machine-interaction. The transparent nature of the sensor makes the described device discreet, hence attractive for applications that require a sensor worn on the face (e.g. stroke rehabilitation, emotion monitoring).

BRIEF DESCRIPTION OF THE DRAWINGS

FIG. 14A: The strain values are shown above the corresponding peaks.

Each strain was applied for 1 minute, released for 30 seconds, and repeated 3 times for a device with a 100 μm height and 100 μm width probe channel, 2×LR region filled with IL1. FIG. 14B: Relative resistance change (ΔR/R) under different percentage strains for 1×, 2×, and 4× and their respective GF values obtained by the linear fit of the plot. Dashed lines show the strain threshold for each device obtained from the interception of the fitted line with the x-axis.

FIGS. 15A-F show according to an exemplary embodiment of the invention the resistance response over time to an increasing and decreasing strain step function from 0% to 18%, 1.4% increments with holding duration 5 s, 10 s, and 45 s (FIGS. 15A-B). ΔR-strain graphs. Hysteresis graphs for FIG. 15C 5 s, FIG. 15D 10 s and FIG. 15E 45 s waiting time per step. The continuous line represents the increasing steps (Up) and the dashed line the decreasing steps (Down). FIG. 15B: Cyclic response to a 0.1 Hz sinusoidal strain function (from 1% to 7%) after an initial 15 minutes of stabilization. FIG. 15F. Strain threshold—Normalized volume threshold graph. Normalized volume-threshold corresponds to volume threshold ($V_{ST}$) to ΔV/strain ratio. $V_{ST}$ corresponds to the volume of connecting channel between air reservoir and sensing channel.

DETAILED DESCRIPTION

Mechanical Input to Liquid Displacement to Electrical Resistance Conversion

Figure 1:
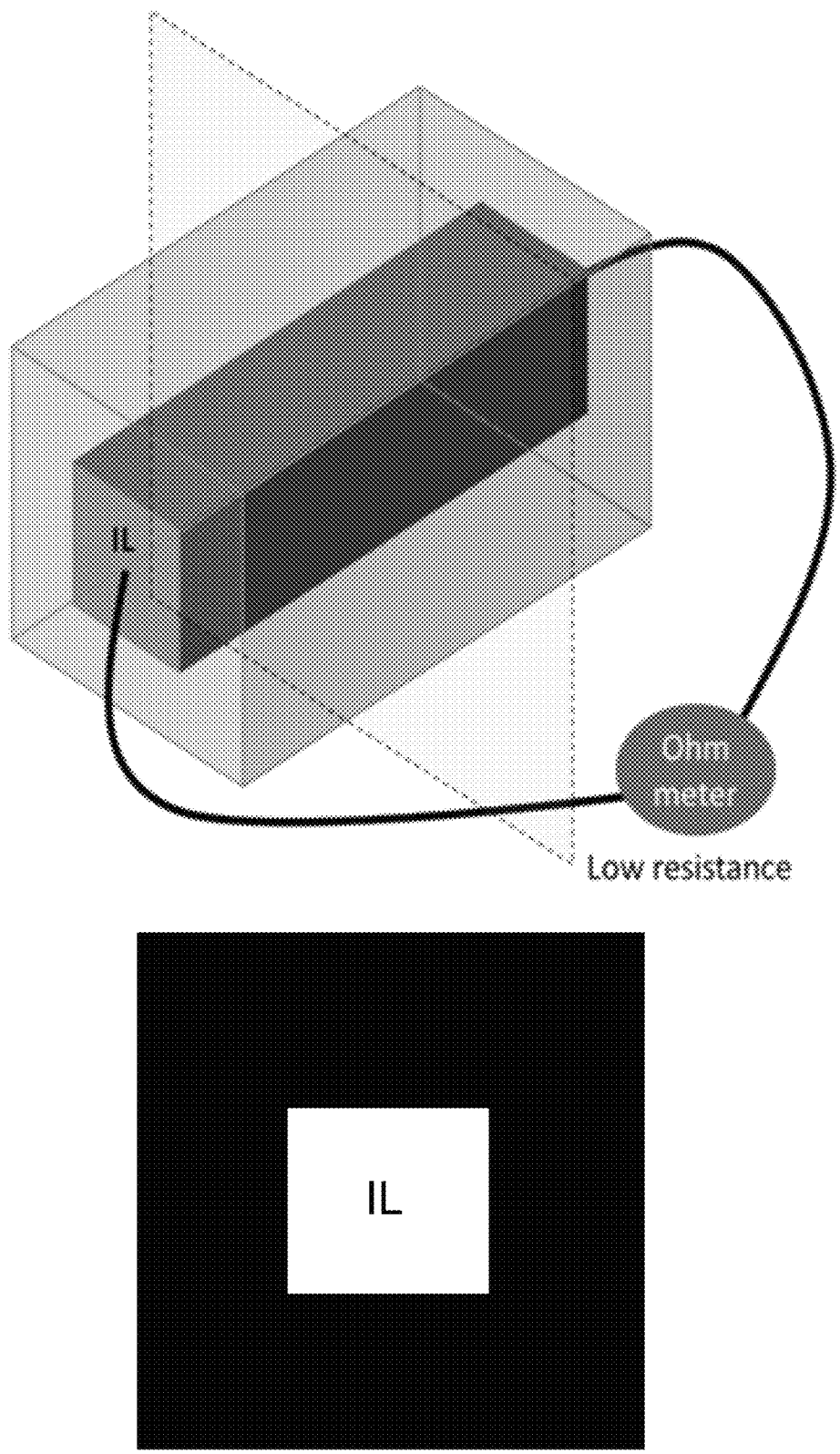
FIG. 1 shows according to an exemplary embodiment of the invention a 3D schematic of a microfluidic channel filled with an ionic liquid (IL). Two electrodes are used to measure the resistance via an ohmmeter. The resistance is low due to the large cross-section area of the IL. The cross-section shape of the channel filled with IL is shown below.

When a microfluidic channel is filled with a conductive liquid (e.g. ionic liquid (IL)) (FIG. 1), the resistance of the channel is determined by the resistivity constant of the liquid, liquid channel length and the liquid cross section area.

Figure 2:
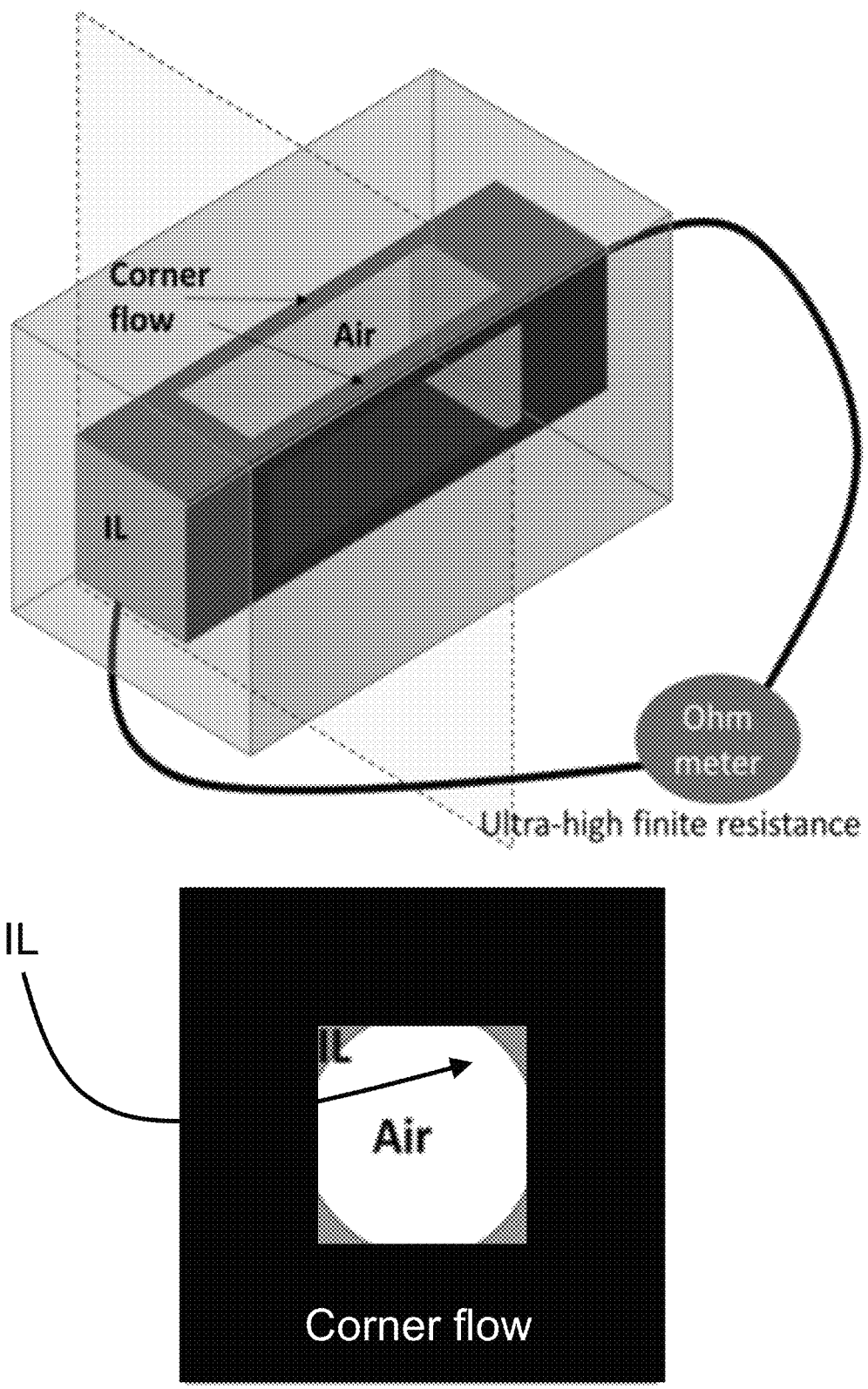
FIG. 2 shows according to an exemplary embodiment of the invention a 3D schematic of a microfluidic channel filled with an ionic liquid (IL) with an air bubble inside. Two electrodes are used to measure the resistance via an ohmmeter. The resistance is high but finite due to the smaller cross-section area of the IL and the corner flow in capillary channels. The cross-section shape of the IL channel with an air bubble is shown below.

Therefore, any change in the cross-sectional area of the liquid (or the channel) will induce a resistance change. The inventors have found that when an air bubble is introduced in a microfluidic channel with rectangular profile filled with a low surface energy liquid, the corner flow in the rectangular channels provides a continuous liquid connection between the two sides of the air bubble, which in turn provides a way to continuously monitor the resistance (FIG. 2). The introduced air bubble drastically decreases the cross-section area of the liquid segment, providing the ultrahigh sensitivity.

Figure 3:
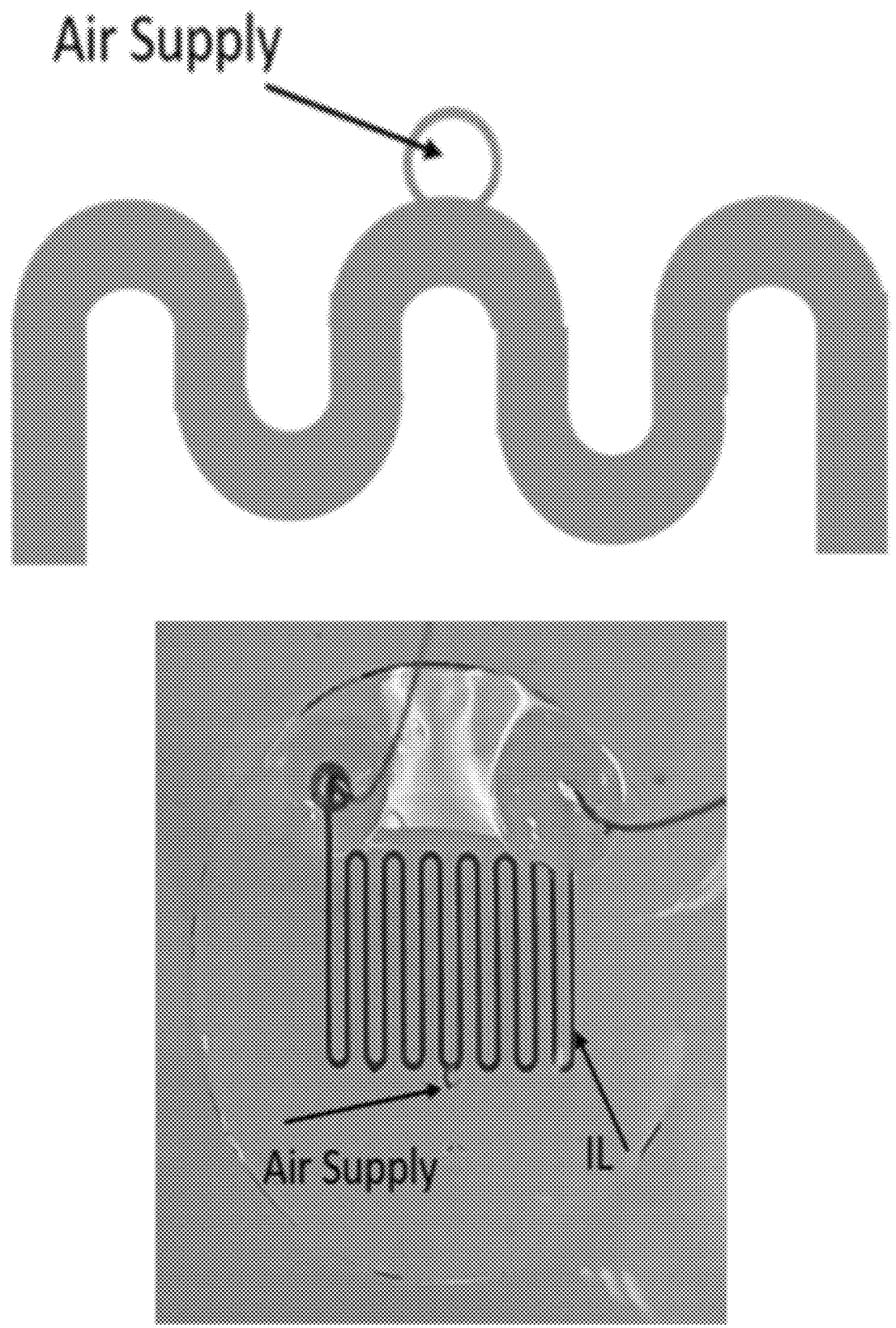
FIG. 3 shows according to an exemplary embodiment of the invention a top view schematic of a serpentine shaped microfluidic channel filled with an ionic liquid (IL) with an open-air supply on top. The fabricated device is shown on the bottom. Two electrodes are used to measure the resistance via an ohmmeter.
Figure 13:
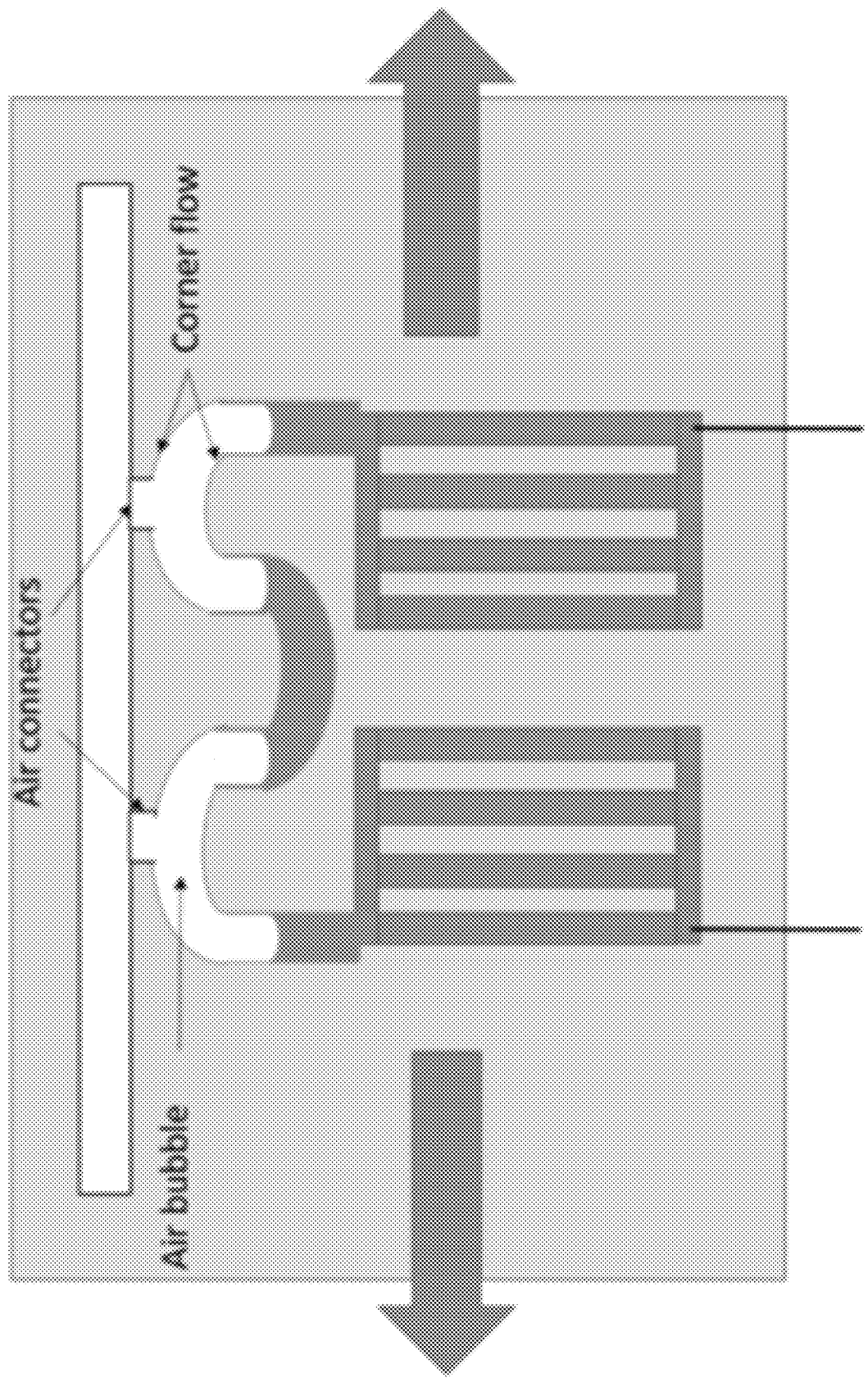
FIG. 13 shows according to an exemplary embodiment of the invention that when the strain is increased, the air volume injected into the serpentine channels increase. This results in a longer air bubble and longer corner flow connection. Compared to the completely filled microfluidic channel, a microfluidic channel that is connected by the corner flow has much smaller liquid cross-section area hence much larger resistance.
Figure 14A:
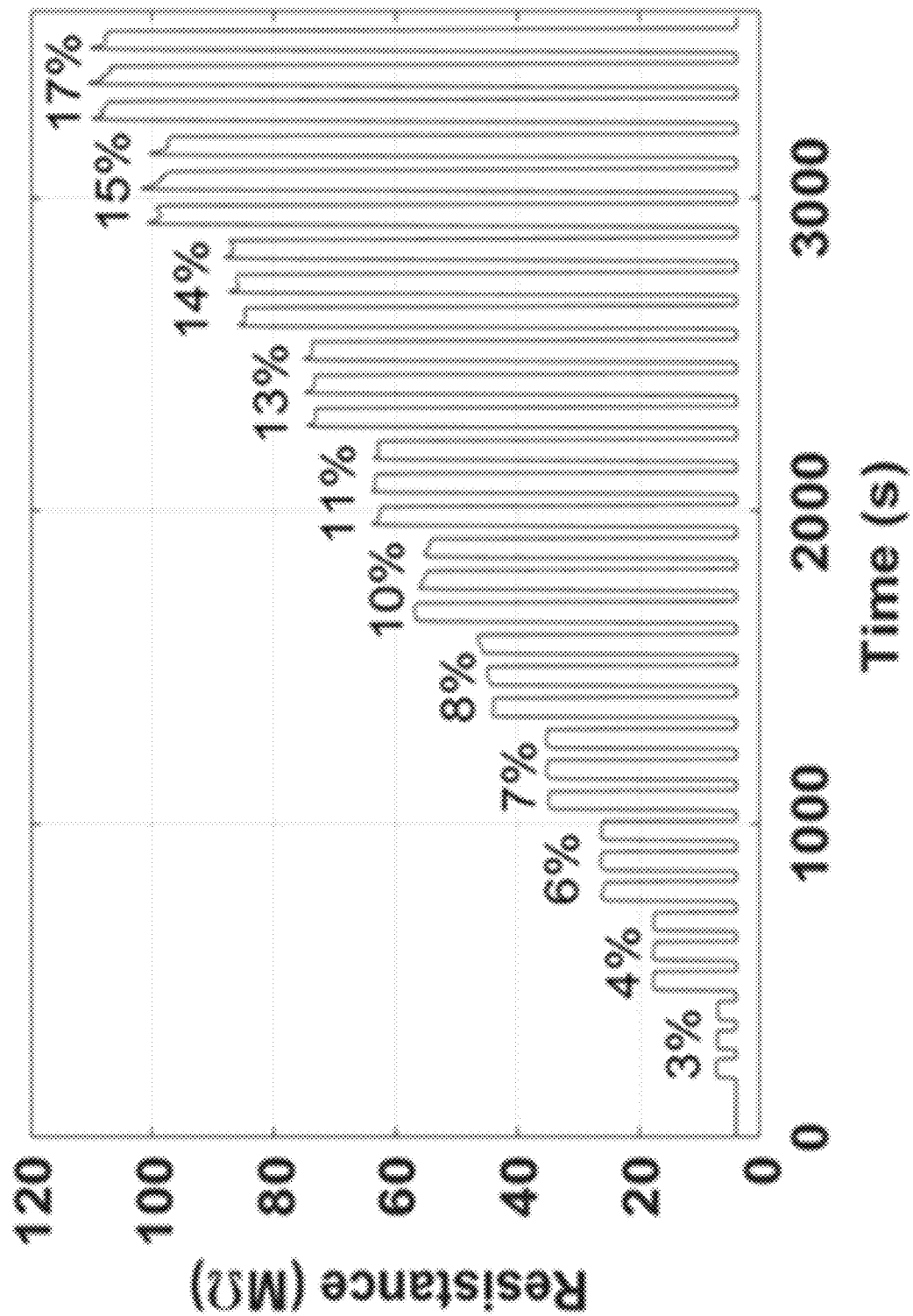
FIGS. 14A-B show according to an exemplary embodiment of the invention representative graphs of the resistance versus time in response to increasing strain.
Figure 14B:
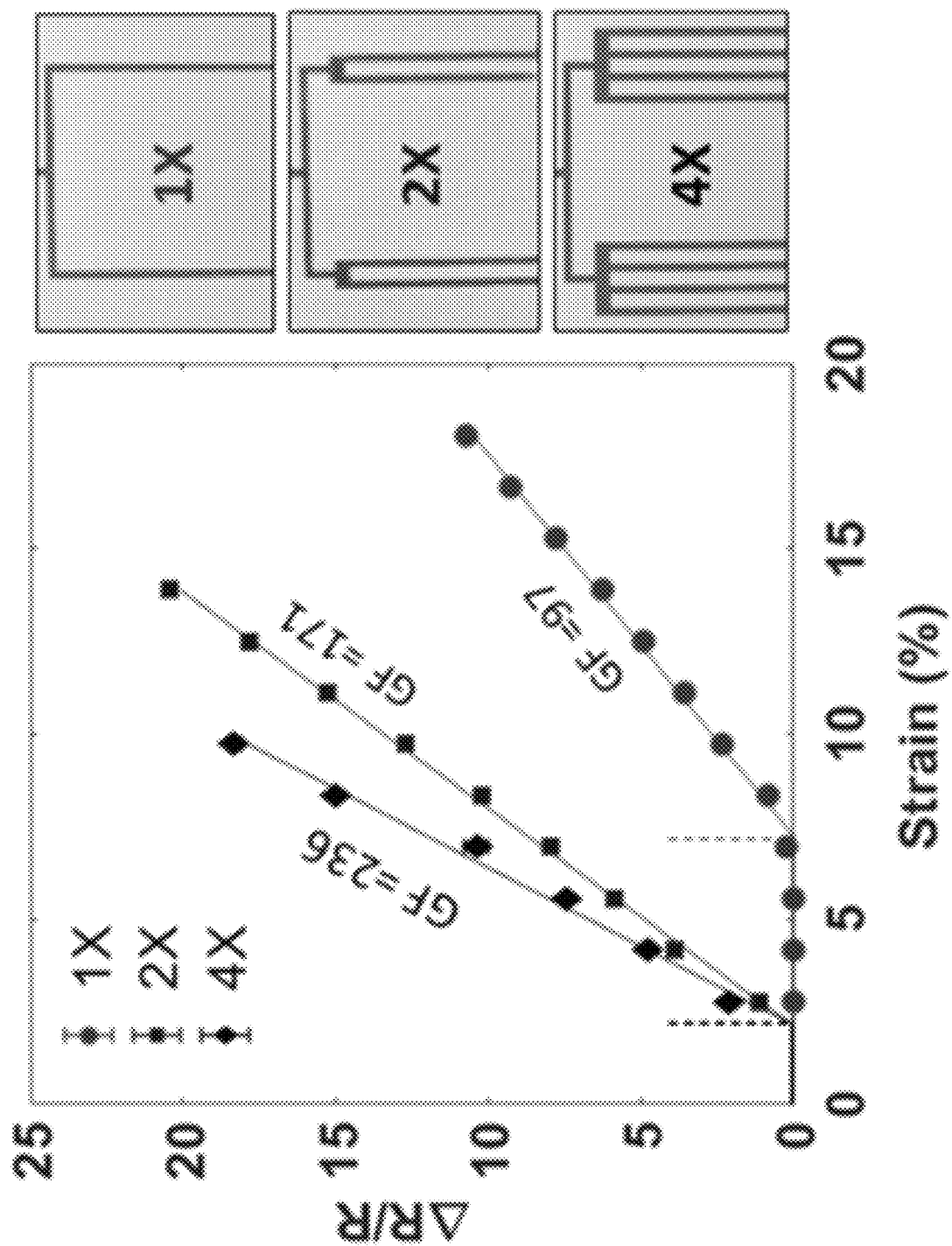

In one embodiment, there is a microfluidic circuit structure where an air bubble is formed inside a microfluidic channel, as a result of the applied linear strain. FIG. 3 shows the schematic of a device which converts the liquid displacement into large resistance change and a device fabricated using this strategy. The inventors have utilized Mach-1, Biomomentum Inc., mechanical tester or a biaxial strain actuation system (Bi-SAS) developed in-house to characterize dilatometric sensors. The devices are attached to the Mach-1 by fixing them from two sides on the two fixtures of the instrument (as shown in FIG. 13 of Appendix B in U.S. Provisional Patent Application 62/914,430 filed Oct. 12, 2019 to which this application claims priority). The blue arrows indicate the direction of the fixture 1 movement.

Figure 4:
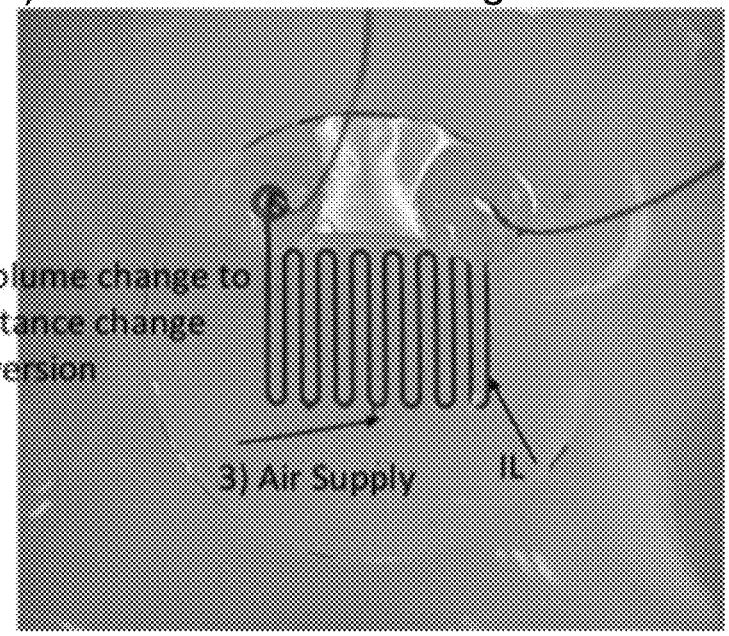
FIG. 4 shows according to an exemplary embodiment of the invention a fabricated 200 μm wide serpentine shaped microfluidic channel filled with an ionic liquid (IL) under the strain (strain direction is shown with the double arrow). The corner flow at the location of the air bubble is shown on the image. The image on the bottom right shows the zoomed-in region of the channel with the around the air supply. The air bubble and corner flow (blue tinted channel walls) is clearly visible. For color images and interpretation of FIG. 4, the reader is referred to FIG. 4 of Appendix A in U.S. Provisional Patent Application 62/914,430 filed Oct. 12, 2019 to which this application claims priority.
Figure 4:
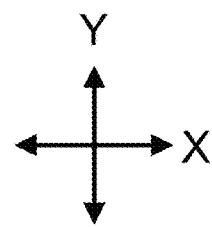
Figure 4:
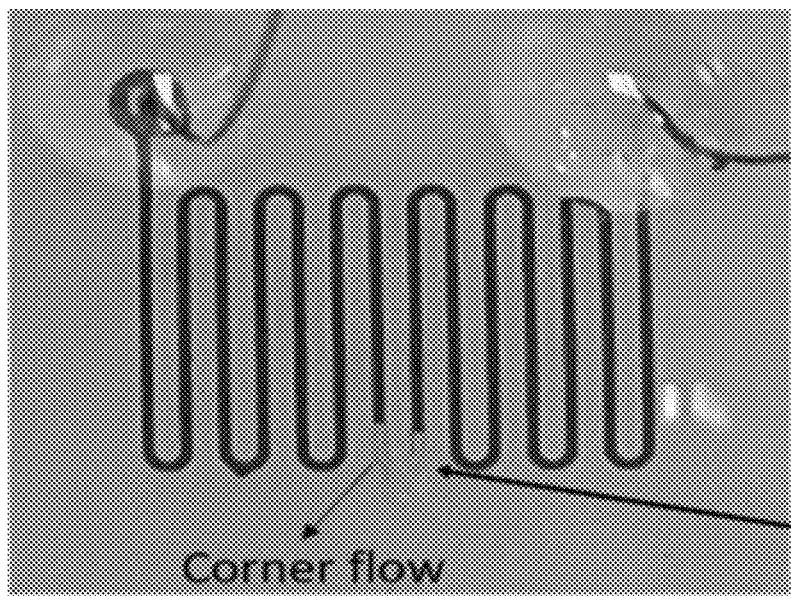
Figure 4:
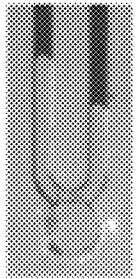
Figure 4:
Figure 5A:
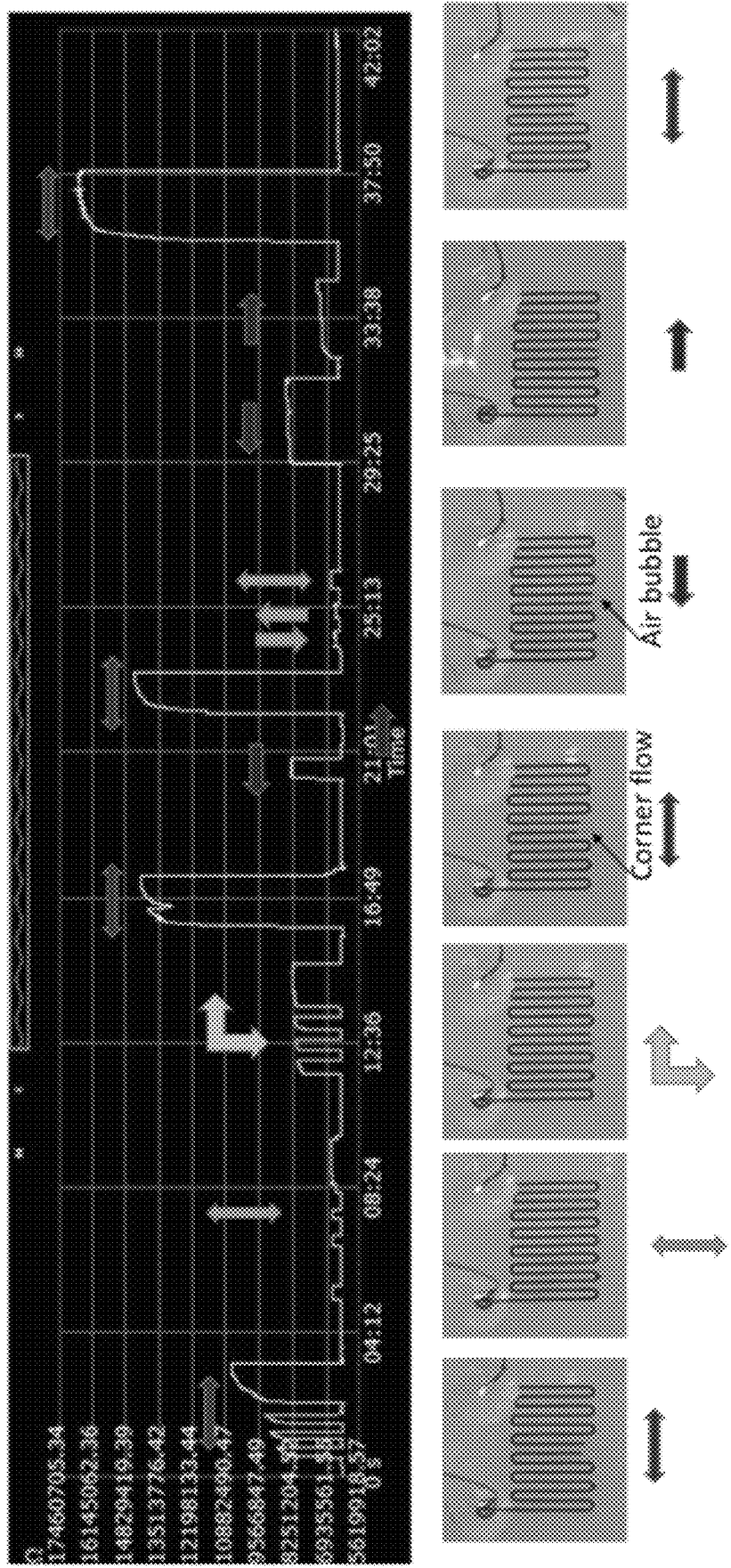
FIGS. 5A-B show according to an exemplary embodiment of the invention real time recorded resistance of the fabricated device (top in each example) during various strain directions ($\varepsilon = \sim 20\%$) and associated images of the device (bottom in each example). The arrows show the direction of the strain (x-, y-, or biaxial). The last image and signal in the bottom example correspond to an applied strain of 40%. For color images and interpretation of FIGS. 5A-B, the reader is referred to FIG. 5 of Appendix A in U.S. Provisional Patent Application 62/914,430 filed Oct. 12, 2019 to which this application claims priority.
Figure 5B:
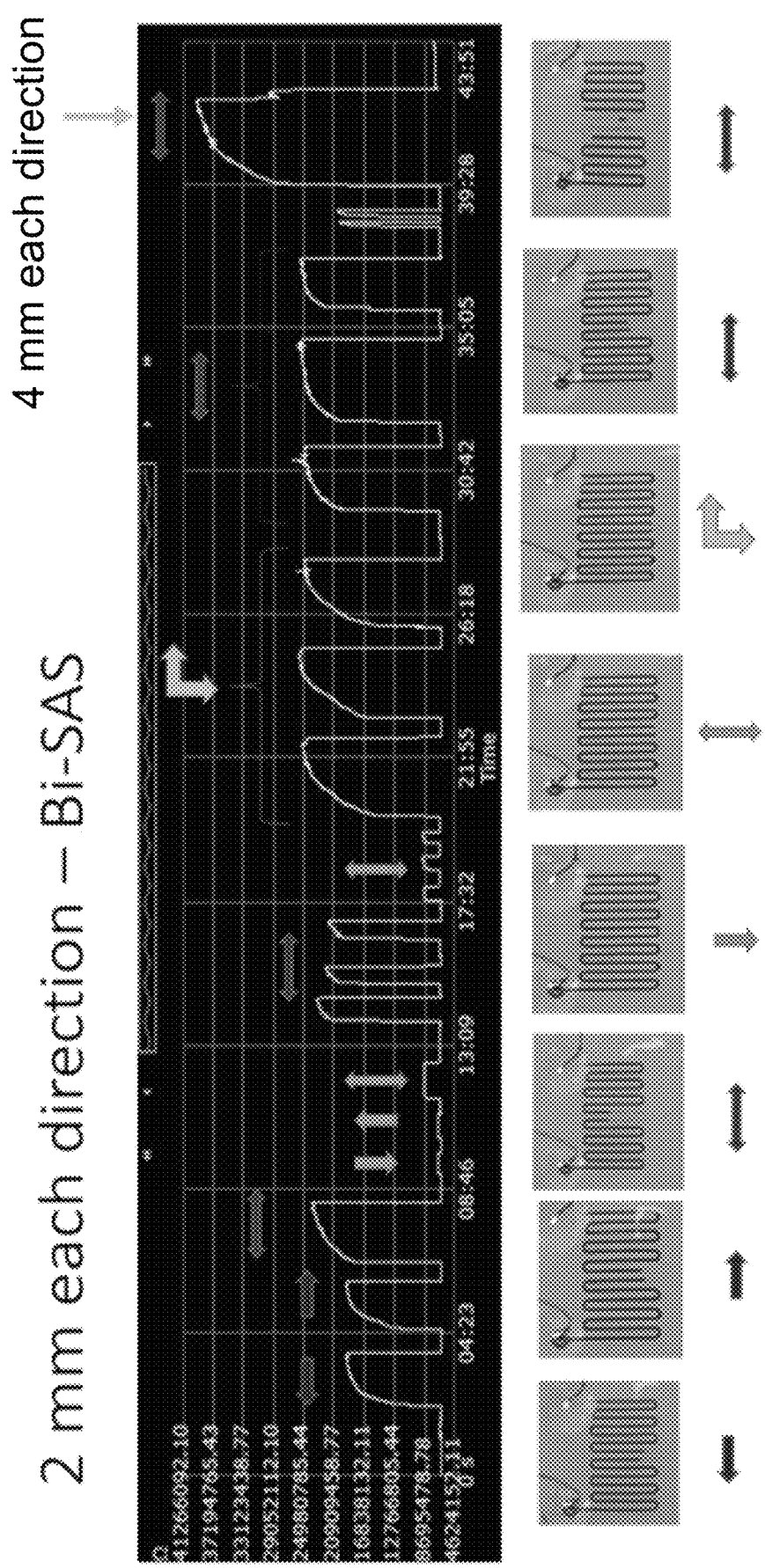

To apply the strain, the distance between the fixtures is increased, which stretches the device in perpendicular to the channel network elongation. When strain is applied to this device in this configuration, an air bubble is formed around the two sides of the air supply due to the dilatation of the microfluidic network. FIG. 4 shows the device being tested on a Bi-SAS before applying strain and after applying strain. The two menisci on each side of the air supply is connected through corner flow as indicated in FIG. 4. The resistance is continuously monitored during this test. A large resistance change proportional to the liquid displacement was observed when strain in perpendicular direction to the serpentine channels is applied to the devices. In contrast, when the strain direction is reversed (strain is parallel to the serpentine channel elongation), no air bubble formation and liquid displacement is observed. The real time resistance response obtained using an ohmmeter is shown in FIGS. 5A-B. The strain in the x-direction (red arrows show the x-direction; for color images and interpretation of FIGS. 5A-B, the reader is referred to FIG. 5 of Appendix A in U.S. Provisional Patent Application 62/914,430 filed Oct. 12, 2019 to which this application claims priority) causes a significantly larger effect for the sensor in this configuration. The effect is reproducible. In FIGS. 5A-B, the image of the sensor at each strain configuration is shown below the screenshot of the real time ohmmeter data. The blue arrows show the strain in y-direction and the response of the sensor is much smaller for this direction.

Figure 6:
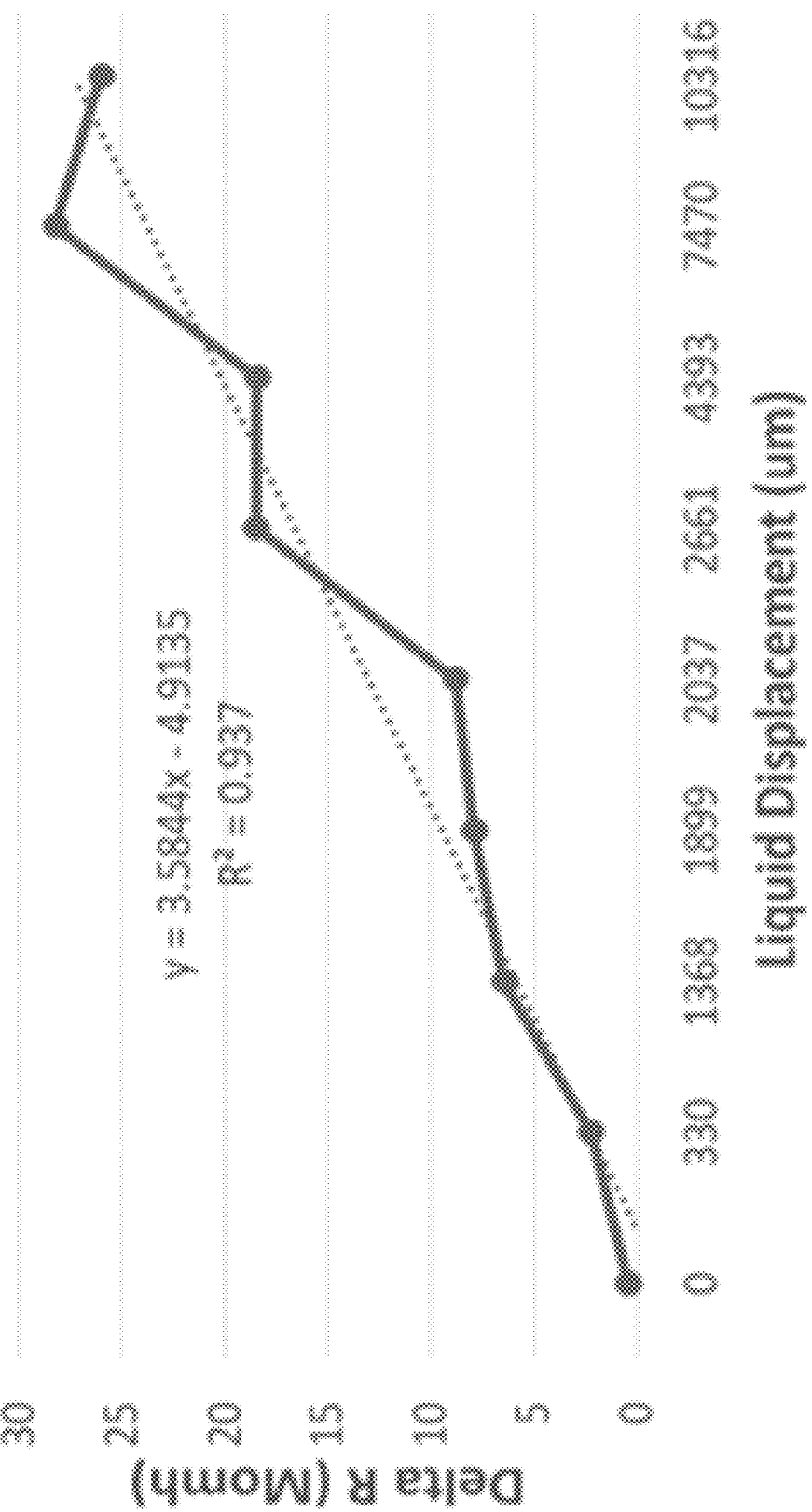
FIG. 6 shows according to an exemplary embodiment of the invention liquid displacement versus resistance change. The slope gives sensitivity of 3.6 MΩ/mm for a 200 μm wide channel.

FIG. 6 shows the liquid displacement versus the ΔR. A linear dependence is observed with a sensitivity of 3.6 MΩ/mm for a 200 μm wide and 100 μm high channel.

Figure 7:
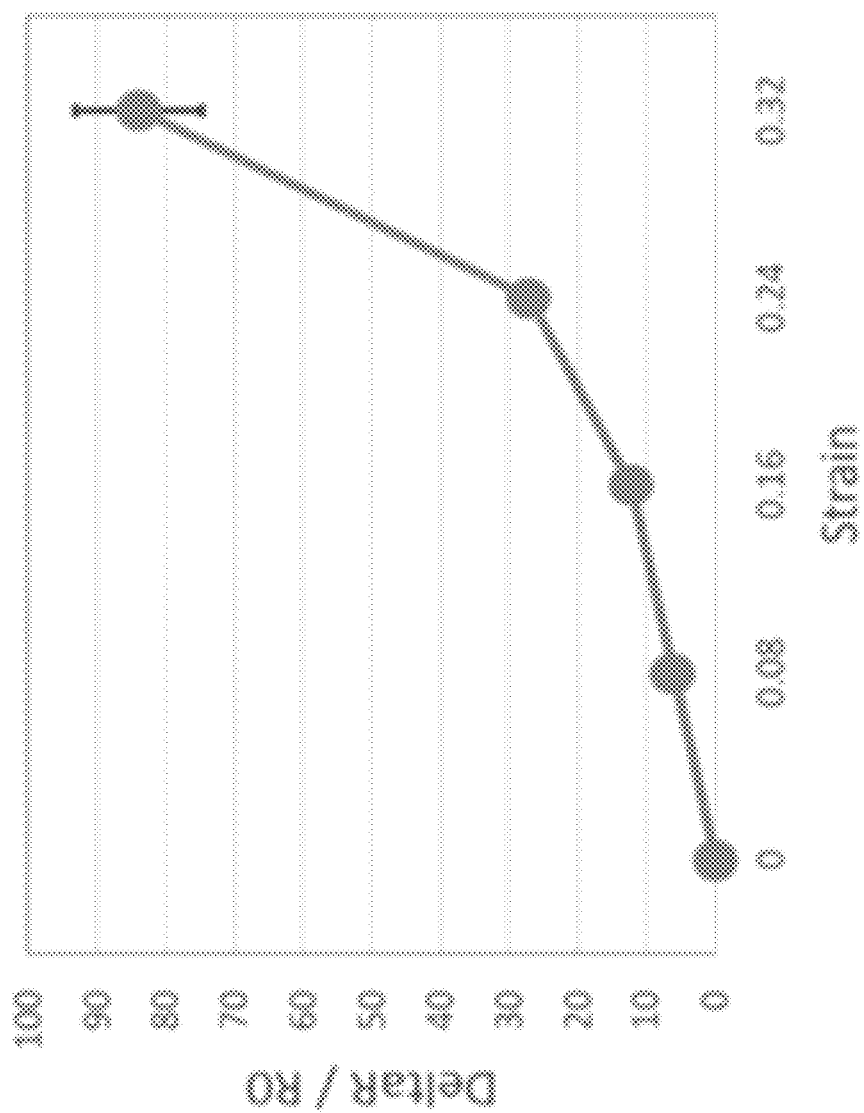
FIG. 7 shows according to an exemplary embodiment of the invention an image of the sensor with 50 μm serpentine channel (top) and sensor under 30% strain (bottom). The $\Delta R/R_o$ versus strain graph is shown in the right. The gauge factor is 240.
Figure 7:
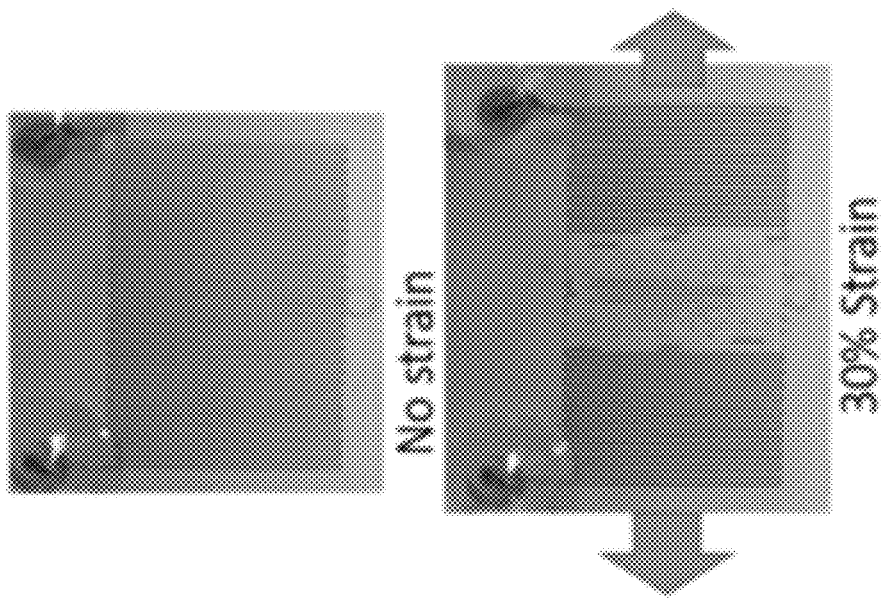

When the channel width is decreased to 50 μm, the sensitivity increases dramatically to 25 MΩ/mm. The resulting gauge factor is 240. FIG. 7 shows the microfluidic strain sensor under test and the $\Delta R/R_o$ versus strain graph.

Figure 8:
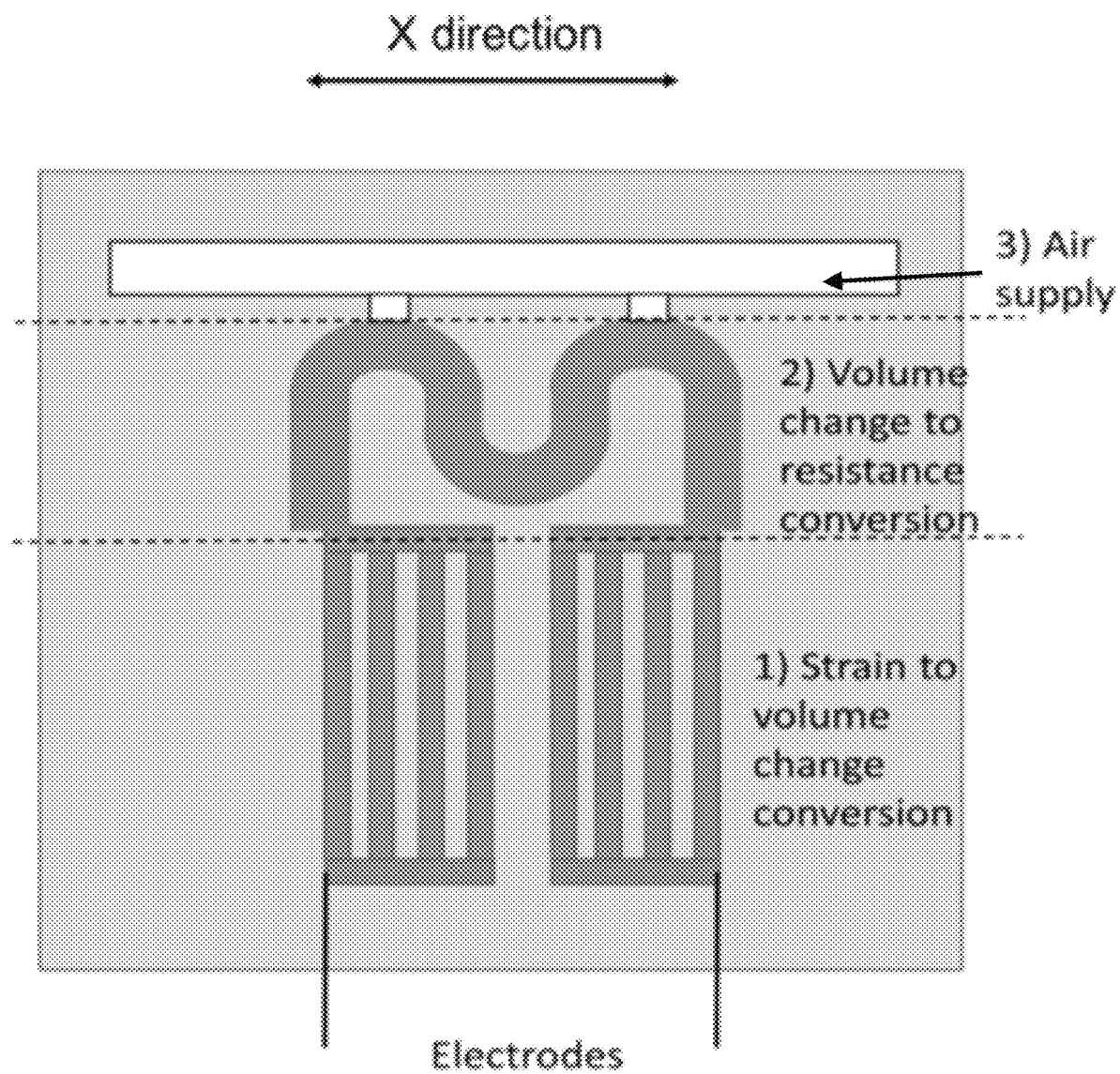
FIG. 8 shows according to an exemplary embodiment of the invention a schematic of the linear strain sensor for enhancing the sensitivity, dynamic range and linearity.

This concept design can be improved by adding elements to increase the strain sensitivity and providing multiple access paths to air supply to increase the dynamic range and linearity. Such an exemplary design is shown FIG. 8. The design has three sections.

Section 1 has narrow microfluidic channels which are parallel to each other. This section converts the linear strain perpendicular to the channel length into a volume change. Therefore, it is responsible for increasing the strain sensitivity. The narrow parallel channels increase the total volume without increasing the total resistance and without membrane collapses. This section is divided into a left part and a right part. The total resistance of the left part is R/n. Here, R is the resistance of one of the narrow channel segments and n is the number of parallel channels in the left part. Similarly, the resistance of the right part is R/m. If n=m, then total resistance of section 1 is 2R/n.

Section 2 is a serpentine or linear shaped channel connecting the left and right parts of Section 1. The length of the channel will increase the dynamic range. Larger width of this section will result in smaller initial resistance. Smaller width will increase the sensitivity. The total resistance of the serpentine channel is Rs. The total initial resistance is Rs+2R/n.

Figure 15C:
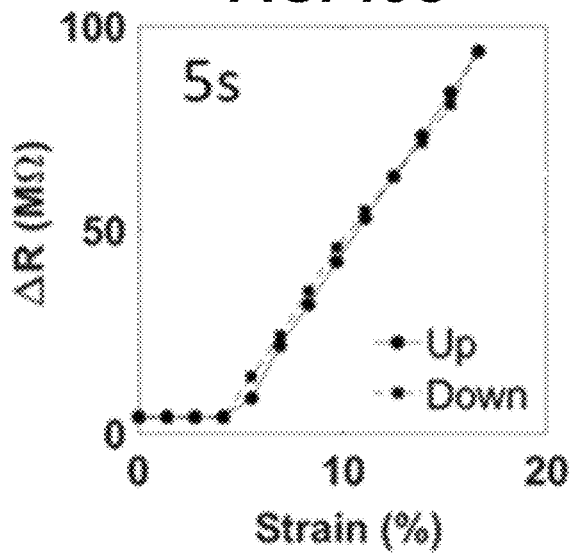
Figure 15D:
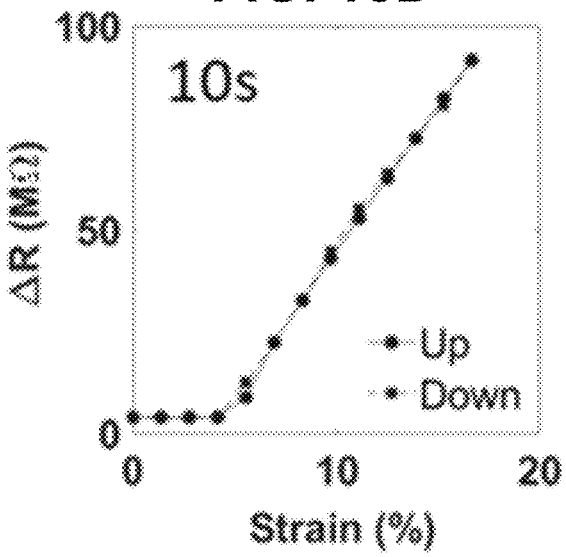
Figure 15E:
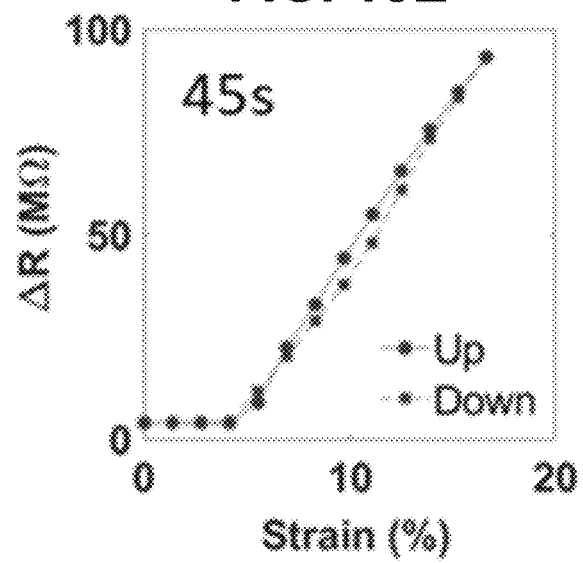
Figure 15F:
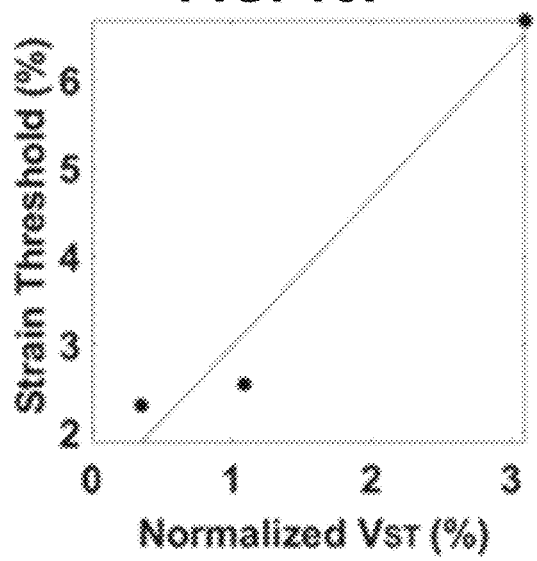

Section 3 is an air supply, which is a wide microfluidic channel filled with air at atmospheric pressure. Air supply is connected to the Section 2 through short narrow channel segments. These connecting segments can be designed as burst valves, allowing the liquid to stay in Section 2 at all times. The volume of these connecting segments determine the minimum strain threshold that is required for dilatometric response as an additional performance control parameter as shown in FIG. 15F.

When a linear strain perpendicular to the microfluidic channel elongation is applied by stretching the device in the X-direction (as shown in FIG. 13 of Appendix B in U.S. Provisional Patent Application 62/914,430 filed Oct. 12, 2019 to which this application claims priority), the microfluidic channel network volume in Section 1 increases. This volume increase is proportional to the amount of the strain.

Figure 9:
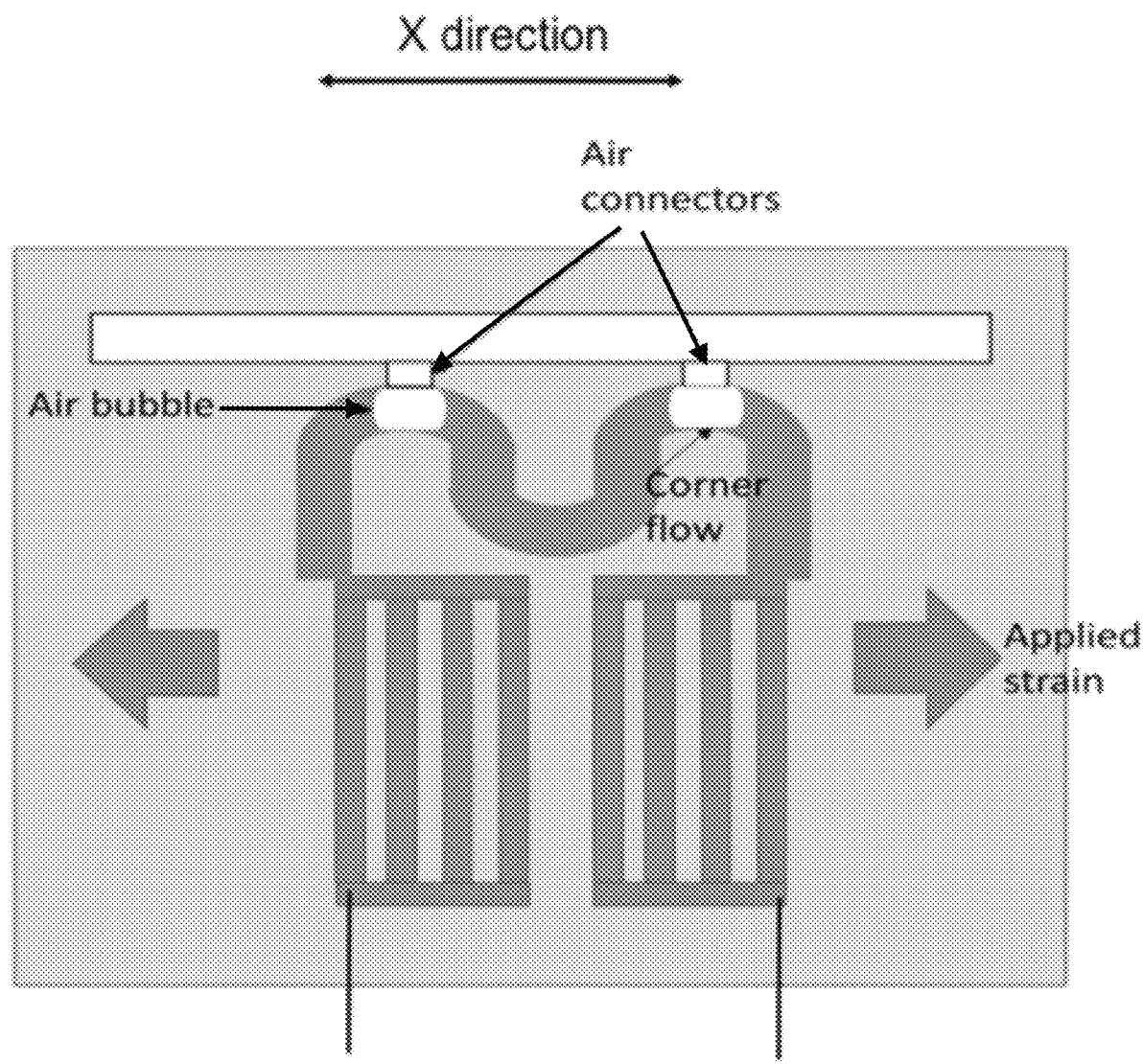
FIG. 9 shows according to an exemplary embodiment of the invention a schematic of the linear strain sensor under strain. The air bubbles and corner flow connection are shown on the schematic.

The volume increase causes a decrease in the pressure inside the microfluidic network hence pulls air into the Section 2 from Section 3. This behavior is analogous to a syringe operation; when the plunger of a syringe is moved in the outward direction, the air fills the syringe, assuming the syringe tip is in ambient air. In the case of this invention, the Section 1 is analogous to a syringe plunger, Section 2 is analogous to a syringe liquid reservoir and Section 3 is analogous to a syringe tip in ambient air. The application of strain is analogous to movement of the syringe plunger outwardly. The air bubble entering Section 2 from Section 3 because of the applied strain is shown in FIG. 9. As the strain magnitude in the x-direction is increased, the volume of the air entering into the Section 2 from Section 3 increases, which increases the length of the air bubble. When air bubble is injected, the ionic liquid recedes towards Section 1, leaving a residual ionic liquid behind at the corners of the microfluidic channel. The residual ionic liquid prefers the corners because of the increased surface interactions at the corners. This residual ionic liquid is called corner flow. As the length of the air bubble increases, the length of the ionic liquid connection through the corner flow also increases. FIG. 13 shows the increase of the air bubble length and corner flow region due to the increased strain. There is a linear relation between the displaced liquid (air bubble length) and resistance change as shown in FIG. 6.

Mechanical Input to Liquid Displacement to Optical Domain Conversion

Figure 10:
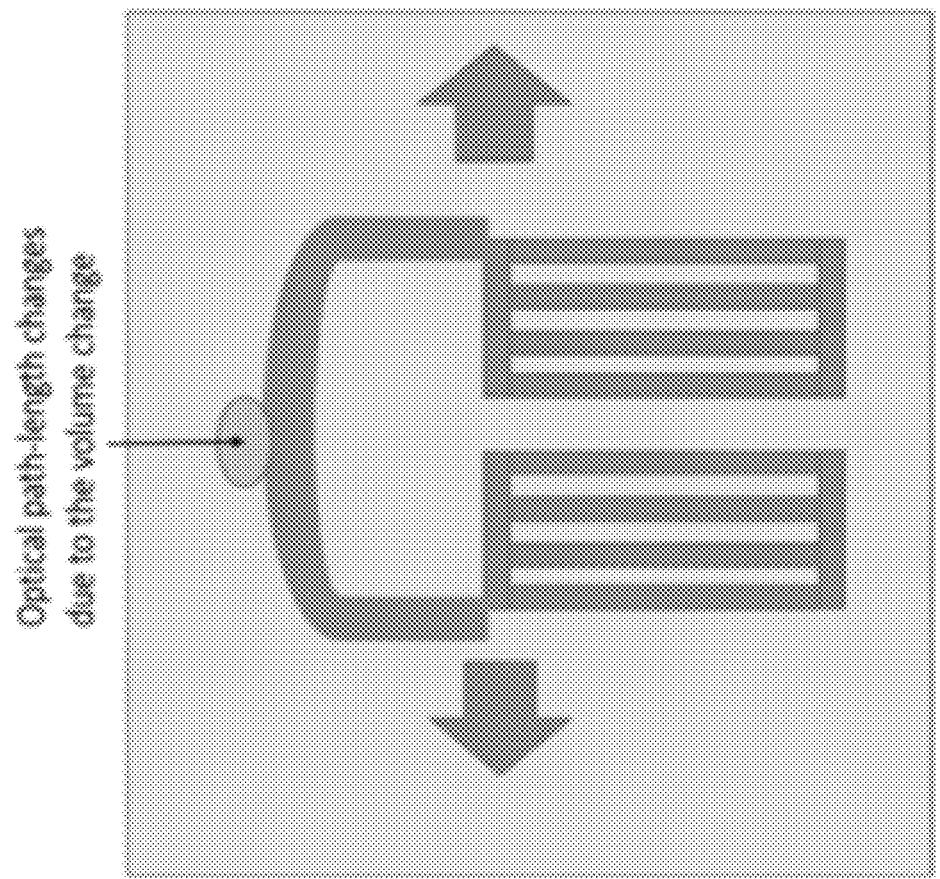
FIG. 10 shows according to an exemplary embodiment of the invention a schematic of an optical dilatometric linear strain sensor, neutral (left) and when under strain (right). The change in the liquid volume inside the optical element can be detected with a wearable device.
Figure 10:
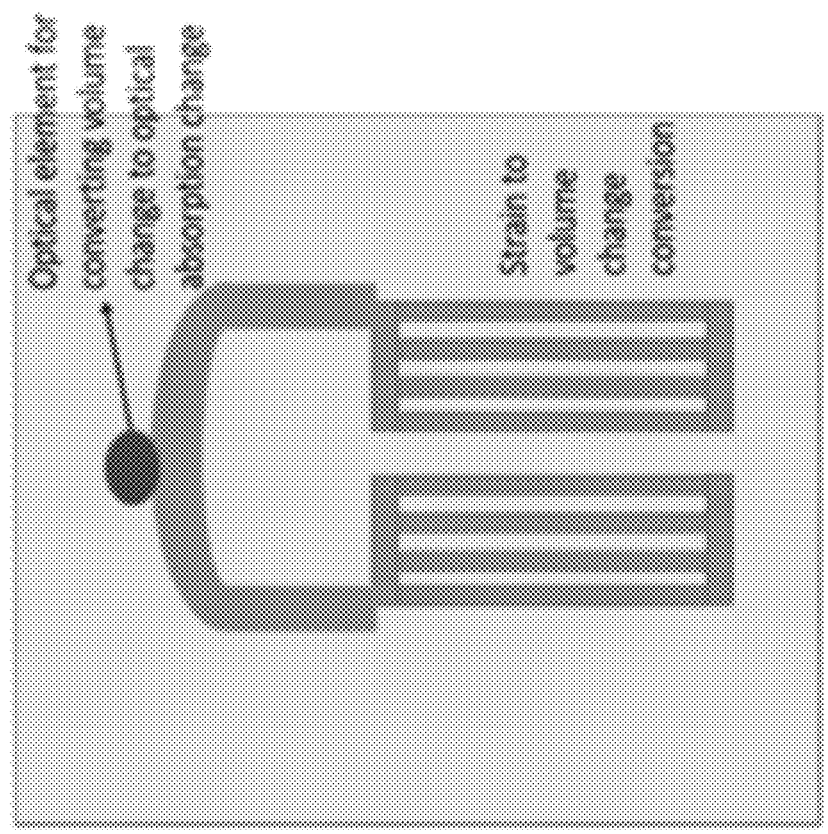

Utilizing optical signals in wearable devices has advantages such as simplifying the data transfer, ability to use soft materials and providing immunity to electromagnetic interference. The dilatometric mechanical sensors can be configured to induce large optical parameter changes (i.e. absorption, reflection, fluorescence) due to the liquid displacement. An optical element, instead of an electrical resistance element should be added to the Section 1 to convert the liquid displacement into an optical signal. An example design is shown in FIG. 10.

Figure 11:
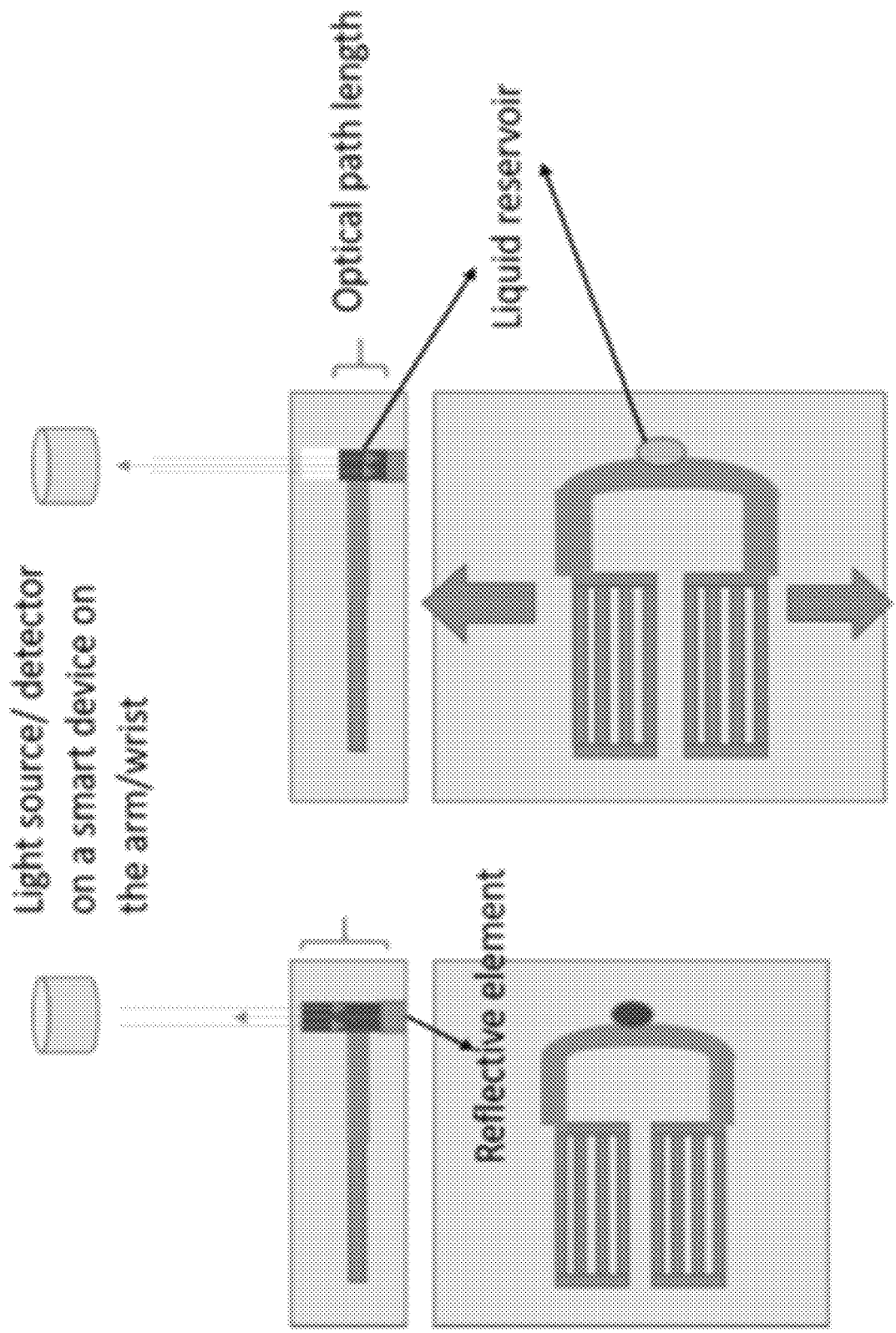
FIG. 11 shows according to an exemplary embodiment of the invention a schematic of the side view (top) of the optical dilatometric linear strain sensor, neutral (left) and when under strain (right). The corresponding top view is shown on the bottom. The change in the liquid volume inside the optical element causes a change in the optical path length of the light propagating inside the optical element. This can be detected by an LED/optical detector pair.

Here, when strain in the x-direction is applied, the liquid displacement causes a reduction of the liquid volume in the optical element. In this case, the liquid can be any liquid with a strong optical absorption band in the electromagnetic spectrum such as ethylene glycol mixed with a blue dye. The side view of the device describing the interrogation mechanism is shown in FIG. 11.

Variations to the Embodiments

So far, the sensor configurations for detecting linear strain are described. In these configurations, the parallel microfluidic channels run perpendicular to the direction of strain that is being measured. Embodiments of this invention can also be used for biaxial, multiaxial and area-strain measurements. For measuring the multiaxial strain (or area-strain), microfluidic channels with circular symmetry has to be used. For example, Section 1 has to be modified as concentric rings, Section 2 has to be modified as a circular serpentine channel and Section 3 as a circular ring.

To increase the cross-section area contrast between a filled channel and a channel with air bubble, the cross-section profile of the channel can be modified. For example, reducing the number of corners will provide larger contrast. Triangular channel shape or a hemi-circle channel shape can be used to provide three or two corners, respectively.

Figure 12:
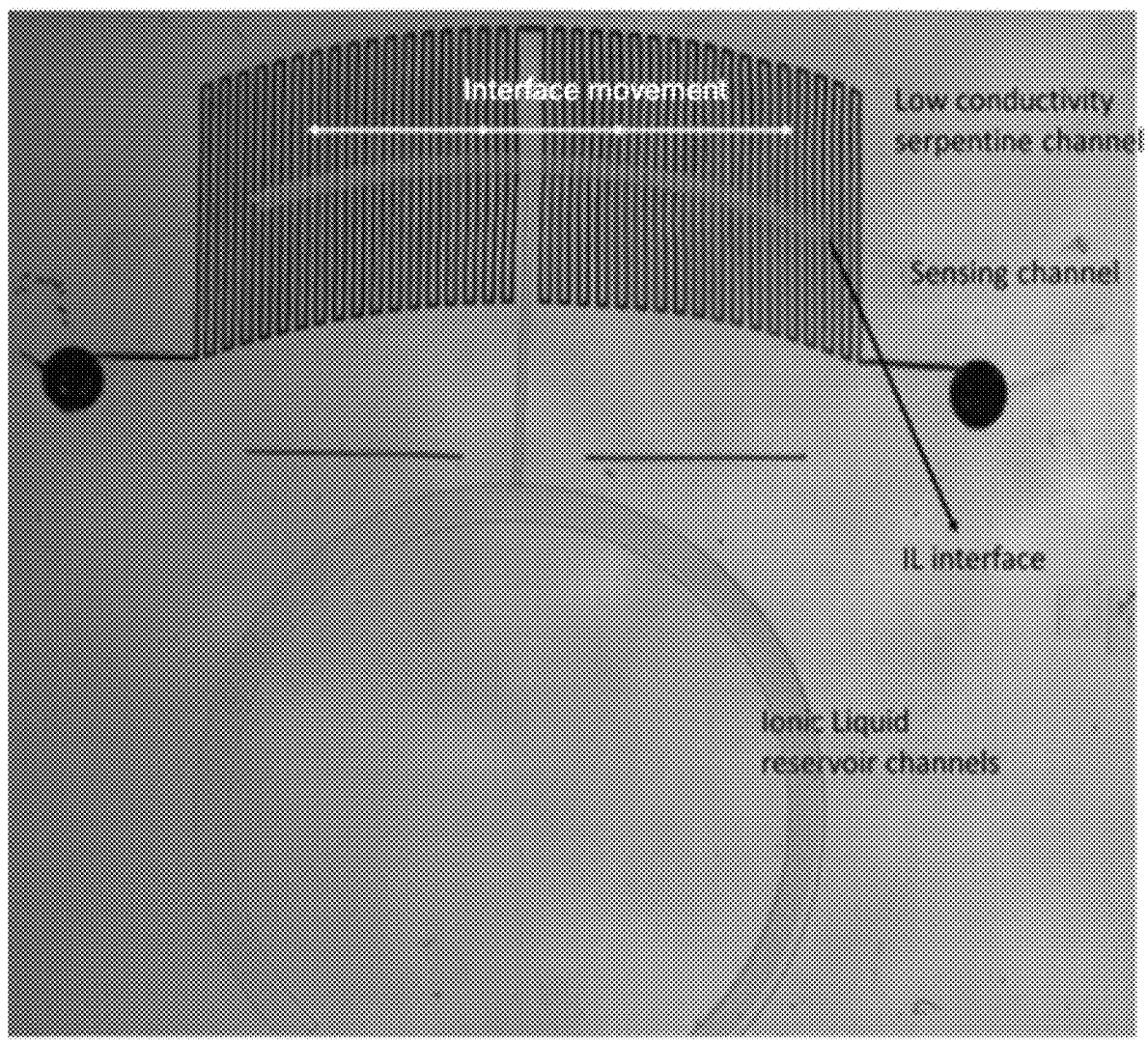
FIG. 12 shows according to an exemplary embodiment of the invention a photograph of a sensor with another configuration for converting the liquid displacement to resistance change. The IL (blue region) inside a microfluidic channel and the CB/PDMS channel are in contact with each other. For color images and interpretation of FIG. 12, the reader is referred to FIG. 12 of Appendix B in U.S. Provisional Patent Application 62/914,430 filed Oct. 12, 2019 to which this application claims priority.

In addition to the utilization of corner flow, a hybrid material approach can be utilized to convert the liquid displacement to the resistance change. For example, a carbon black (CB)/PDMS material can be patterned as a serpentine channel as shown in FIG. 12. In this configuration, the microfluidic channel and the serpentine CB/PDMS channel are fabricated as different layers. The liquid inside the microfluidic channel creates a meniscus inside the CB/PDMS layer in contact with the CB/PDMS. The electrodes are connected to the two sides of the CB/PDMS channel (black circles in FIG. 12). The total resistance of the CB/PDMS section is chosen to be large for higher gauge factor. When the high conductivity ionic liquid advances on the sensing channel it effectively short circuits the vertical CB/PDMS segments reducing the resistance. When the meniscus recedes to the center, the resistance increases.

Device 2 as described supra for optical domain conversion can be configured in planar configuration using waveguides and fiber optic cables. It can also be configured to detect reflection from the liquid meniscus instead of the absorption of the liquid. The optical element can be designed in various shapes instead of a circle.

These mechanical sensors described here can be used for detection of strain, pressure, and flow in various industrial applications. As wearable biosensor devices, they can be used for physical activity assessment and for tactile sensing.

Selection of ionic liquid (IL) is critical for device performance as it directly affects the sensor's response. For instance, properties as viscosity, surface tension, and conductivity contribute significantly to the time response, corner flow morphology, and baseline resistance, respectively. Hence, the selection criteria were based mainly on these factors. Three ILs have been tested: IL1: 1-butyl-3-methylimidazolium trifluoromethanesulfonate ((([BMIM][Otf]), IL2: 1-butyl-3-methylimidazolium dicyanamide ([BMIM][N(CN)2]), and IL3: 1-ethyl-3-methylimidazolium dicyanamide ([EMIM] [N(CN)2]).

Sensors were fabricated following protocols for soft lithography. First, the devices were designed in AutoCAD (Autodesk, Inc.). The master molds with 50 μm and 100 μm height were fabricated following SU-8 2050 photoresist manufacturer protocol and finally, the masters were used to obtain the PDMS (RTV 615) layers by replica molding. The layers are bonded together using plasma bonding.

Once the channels were filled by the desired ionic liquid, plasma was applied to the top surface with a handheld corona gun for 30 s, silver electrodes were placed, and the epoxy was added to seal.

To control the contact angles, the PDMS surface energy was modified by applying plasma.

In an exemplary embodiment, the microfluidic channel dimensions in the range of 50×50 μm$^2$ to 200×100 μm$^2$ (W×H) were tested for both liquid reservoir and sensing channel sections. The devices had an overall footprint larger than 1×1 cm$^2$ and smaller than 5×5 cm$^2$. The overall device thickness was 80 μm to 250 μm. The devices can be bonded to the skin using biocompatible adhesives.

What is claimed is:

1. A method of measuring fluid flow, comprising:
   (a) having a microfluidic network,
      wherein the cross-sectional area of the microfluidic network defines 1 or more corners,
      wherein the microfluidic network contains an ionic or a conductive fluid;
   (b) having an air or a nonconductive fluid supply connected to the microfluidic network, wherein the air or the nonconductive fluid is in contact with the ionic or the conductive liquid;
   (c) applying a strain, a force or a pressure difference to the microfluidic network, wherein the strain, the force or the pressure causes a volume change of the microfluidic network volume, wherein the volume change is proportional to the amount of applied strain, force or pressure, whereby a volume increase causes a decrease in pressure inside the microfluidic network hence pulling an air bubble or a nonconductive fluid into the microfluidic network, and vice versa, wherein (p) the volume of air or the length of the air bubble, or (q) the volume of nonconductive fluid or the length of the nonconductive fluid entering the microfluidic network increases as the applied strain, force or pressure increases, and vice versa, and wherein the air bubble or the nonconductive fluid causes the ionic or the conductive fluid to recede to the 1 or more corners of the microfluidic network and around the air bubble resulting in an electrical resistance change in the microfluidic network; and (d) measuring (p) or (q) which is proportional to the applied strain, force or pressure.

2. A method of measuring strain, comprising:
(a) having a microfluidic network,
  wherein the cross-sectional area of the microfluidic network defines 1 or more corners,
  wherein the microfluidic network contains an ionic or a conductive fluid, and
  wherein the microfluidic network defines a flow direction;
(b) having an air or a nonconductive fluid supply connected to the microfluidic network and wherein the air or the nonconductive fluid is in contact with the ionic or the conductive liquid;
(c) applying a strain to the microfluidic network in a direction perpendicular to the flow direction of the microfluidic network,
  wherein the strain causes a volume change of the microfluidic network volume, wherein the volume change is proportional to the amount of strain applied, whereby a volume increase causes a decrease in pressure inside the microfluidic network hence pulling an air bubble into the microfluidic network, and vice versa,
  wherein the volume of air or the length of the air bubble entering the microfluidic network increases as the applied strain increases, and vice versa, and
  wherein the air bubble causes the ionic or the conductive fluid to recede to the 1 or more corners of the microfluidic network and around the air bubble resulting in an electrical resistance change in the microfluidic network; and
(d) measuring the electrical resistance change in the microfluidic network, wherein the resistance change is proportional to the applied strain.

3. A method of measuring strain, comprising:
(a) having a microfluidic network,
  wherein the cross-sectional area of the microfluidic network defines 1 or more corners,
  wherein the microfluidic network contains an optical fluid, and an optical fluid reservoir, and
  wherein the microfluidic network defines a flow direction;
(b) having an optical fluid open to a constant air pressure reservoir;
(c) applying a strain to the microfluidic network in a direction perpendicular to the flow direction of the microfluidic network,
  wherein the strain causes a volume change of the microfluidic network volume, wherein the volume change is proportional to the amount of strain applied, whereby a volume increase causes a decrease in pressure inside the microfluidic network hence pulling the optical fluid from the optical fluid reservoir into the microfluidic network, and vice versa,
  wherein the volume of optical fluid or the length of the optical fluid entering the microfluidic network increases as the applied strain increases, and vice versa, and
  wherein the optical fluid volume change causes the change in the optical path length in the optical reservoir; and
(d) measuring an absorption change or a reflection change in the optical fluid reservoir, wherein the absorption or reflection change is proportional to the applied strain.

* * * * *